Figure 1:
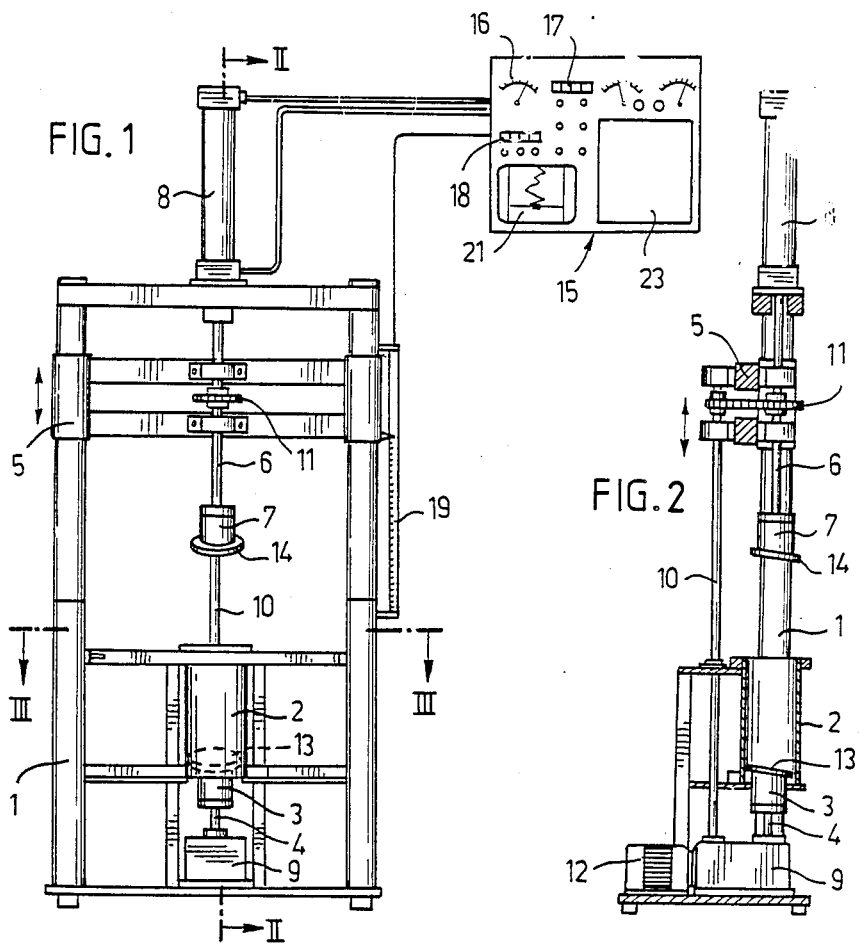

United States Patent [19]

Paakkinen

[11] Patent Number: 4,794,799

[45] Date of Patent: Jan. 3, 1989

[54] METHOD OF AND AN APPARATUS FOR MEASURING THE PROPERTIES, PARTICULARLY THE COMPACTIBILITY OF A STIFF MASS TO BE CAST

[76] Inventor: Ilmari Paakkinen, Moinsalmi, SF-57320 Savonlinna, Finland

[21] Appl. No.: 12,057

[22] PCT Filed: Mar. 27, 1986

[86] PCT No.: PCT/FI86/00033
§ 371 Date: Aug. 3, 1987
§ 102(e) Date: Aug. 3, 1987

[87] PCT Pub. No.: WO86/05883
PCT Pub. Date: Oct. 9, 1986

[30] Foreign Application Priority Data

Apr. 3, 1985 [FI] Finland ................... 851340

[51] Int. Cl.⁴ .............................................. G01N 3/32
[52] U.S. Cl. .......................... 73/803; 73/823; 73/843
[58] Field of Search ............... 73/803, 823, 843, 824

[56] References Cited

U.S. PATENT DOCUMENTS 3,494,172 2/1970 Juve et al. .................. 73/843 X

FOREIGN PATENT DOCUMENTS 2728181 1/1979 Fed. Rep. of Germany .
845097 7/1981 U.S.S.R. ................... 73/803

Primary Examiner—Jerry W. Myracle
Attorney, Agent, or Firm—Michael N. Meller

[57] ABSTRACT

A method of measuring the compactibility of a fresh concrete mass, for obtaining information of the applicability of the mass with respect to the strength properties of the cast product. A sample (20) having a determined weight (m) is taken from the mass and compressed in two opposite directions with a constant force (P) and subjected to a shearing compaction between two slanting planes (13, 14) which extend in parallel with each other and alter their positions through rotation. The volume (V, $V_t$) of the sample is determined at the beginning of the compaction and after a pre-determined compaction work, whereafter the volume change of the sample is compared with experimentally defined limit values. The apparatus comprises a compacting device for subjecting the sample in a container to a shearing compaction, and elements for maintaining the sample under compression during the compaction.

10 Claims, 2 Drawing Sheets

METHOD OF AND AN APPARATUS FOR MEASURING THE PROPERTIES, PARTICULARLY THE COMPACTIBILITY OF A STIFF MASS TO BE CAST

This invention relates to a method of measuring the properties, in particular the compactibility of a stiff mass to be cast, such as fresh concrete mass, wherein a sample having a pre-determined weight is taken from the mass, the sample is exposed to a compaction effect, and the magnitude of a compression of the sample and the work used therefore is determined.

In the concrete industry, technical developments have led to the use of concrete masses which contain water to an ever decreasing degree. This is due to the fact that the lower the water content of the mass, the better the strength values obtained thereby, provided that the other mix proportions of the mass are maintained unchanged. The theoretic optimum amount of water required for hydration is 22 to 40 per cent based on the amount of cement, i.e. the water/cement ratio w/c is within the range 0.22 to 0.40. These so called soil-moist masses are difficult to be shaped and cast also because the present tendency is to grind the cement extremely fine so as to enable a more efficient and rapid utilization of the resulting strength properties of concrete. Such masses are called stiff and semi-stiff.

Soil-moist concrete masses are used mainly in modern slide-mould casting processes. For plastic masses, there exists satisfactory methods and apparatuses for the measurement of the mass properties, compactibility in particular, whereas there are no suitable methods and apparatuses for an accurate measurement of the compactibility of stiff and semi-stiff masses, which is a major disadvantage in the use of concrete masses. The compacter the concrete in the finished cast product is, the higher the strength of the product obtained, and, accordingly, information on the compactibility of a concrete mass to be cast is of great importance for the achievement of an acceptable end result.

The compactibility of a concrete mass is essentially dependent on the stiffness of the mass. If the mass is too stiff, the casting obtained is poorly compacted, containing plenty of air bubbles, whereas too plastic a mass results in low strength values, and further, the shape and tolerances of a product cast without a fixed mould are difficult to control. The compactibility of a mass is not only affected by the amounts and ratios of the different ingredients but also by the quality and size thereof and other such varying factors. Therefore it is important to obtain reliable information on the compactibility of the mass already before the casting thereof.

The plasticity and the compacting properties of plastic concrete masses are nowadays studied by various different methods, among which the following could be mentioned as the most important ones:

Compacting factor test or a measurement of the Mo-value, wherein the concrete mass is caused to pass through a measuring apparatus by means of drop shocks.

Slump test or a depression measurement wherein the mould of a concrete cone compacted in a determined way is removed and the slump formed in the cone is measured.

Remoulding time test or a Vebe-test wherein a slump formed in a conical concrete body is similarly measured but here the slumping is intensified by vibration.

These methods as well as various other ways of examining a mass are suitable for plastic masses and some of them also for so called semi-stiff masses. The stiffer the mass, the worse the possibilities now available for an accurate determination of the mass properties.

With stiff concrete masses it has previously been necessary, for lack of suitable measuring methods and apparatuses, to try to determine the compactibility of the concrete mass to be cast in any particular case even by feeling with hands on the basis of ones professional skill and experience. Such determination of a fresh stiff mass by hands, however, is unreliable and subjective, thus frequently leading in rejected cast products.

The object of this invention is to provide a method which avoids the above disadvantages and enables a more accurate measurement of the compactibility of a stiff mass to be cast. This object is achieved by means of a method according to the invention which is characterized in that the sample is compressed in two opposite directions with a constant force, the sample is subjected to shearing compaction under a constant compression between two slanting planes which extend in parallel with each other and alter their position through rotation, and the volume of the sample is measured at the beginning of the compaction and after certain compaction impulses.

The invention is based on the idea that the determination of the compactibility of a concrete mass is carried out by a machine under accurately uniform conditions which are reproduceable for different samples, whereby the obtained information on the compactibility is always reliable. Finnish Patent Specification No. 64,073 discloses one way of effectively compacting stiff concrete masses, namely a so called shear compaction method. In this measurement, the different parameters, such as the weight of the sample and the pressure exerted on the sample, can be kept constant so that only the composition of the sample varies. In the manufacture of concrete pieces, a test series is carried out with one particular casting machine for the determination of the compactibility measured from the sample, i.e. the density change, and, further, for the determination of the strength of the finished cast products, thus obtaining an upper and a lower limit for the mass compactibility, which limits are specific for this particular casting machine and within which it is easy to succesfully cast these concrete masses into desired products.

By virtue of the method according to the invention it is possible to immediately adjust the composition of the concrete mass to be manufactured in the concrete mixer on the basis of the compactibility determined from a sample so that the density and the fresh strength of the cast product becomes such as desired. In this way it is possible to avoid rejection of finished products as well as wasted work associated therewith. The compactibility of a stiff concrete mass can be examined as accurately as previously has been possible only in the case of plastic masses. Consequently, the method according to the invention is particularly suited for controlling the manufacture of concrete products.

A compactibility measurement according to the present invention results in accurate information on an increase in the density of the sample taken from the mass when the mass is compacted in a precise, pre-determined manner. The density of the sample can be determined continuously during the test by means of conventional calculations when the sample has been weighed and the volume of the mass sample is observed continuously in the test apparatus. Both the final density of the test piece and the density changes at the initial stages of the test are significant for the compactibility.

In order to estimate the quality of the concrete to be cast it is especially important to know how firm the concrete will be after the hydration process has been completed therein. In practice, the quality of concrete is controlled by means of strength test pieces and samples cut out of the finished product.

Forming of strength test pieces from a stiff concrete mass is difficult and unreliable because it is difficult to obtain compact samples by means of the test methods now in use. Vibration sometimes does not result in any compaction at all. Cutting off a sample from a finished product often spoils an expensive, useful product.

This method enables formation of compact test pieces of uniform quality so that the compactibility of stiff masses, too, can be examined. This invention ensures that the compaction of the samples into test pieces is always carried out by a machine under accurately uniform conditions and that the strength measuring results are comparable between different laboratories both with fresh concrete and after the concrete has cured.

The invention also concerns an apparatus for applying the method described above, which apparatus is characterized by comprising a compacting device including two compaction plates, the surfaces of which extend in parallel and which are rotatable around an axis of rotation slantingly positioned with respect to the surfaces of the compaction plates in order to direct a shearing compaction on the sample contained in said container from two opposite directions, and means for pressing one of the compaction plates towards the other compaction plate.

The shearing compaction to be exerted on the sample can be extremely well controlled in this kind of apparatus, so that all measuring results obtained by means of the samples are mutually comparable under uniform measuring conditions.

Figure 3:
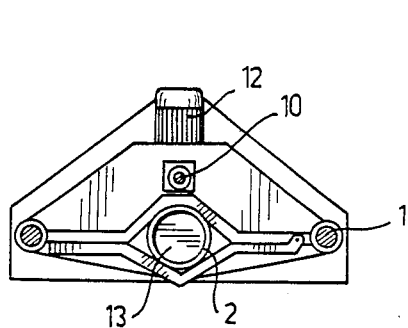
Figure 4:
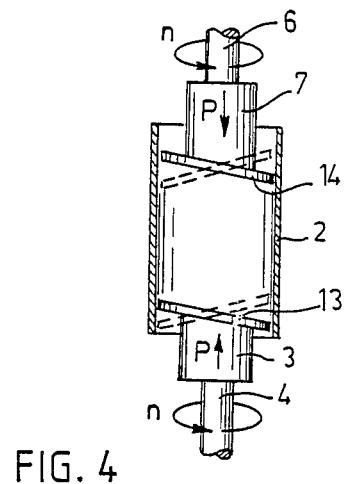
Figure 5:
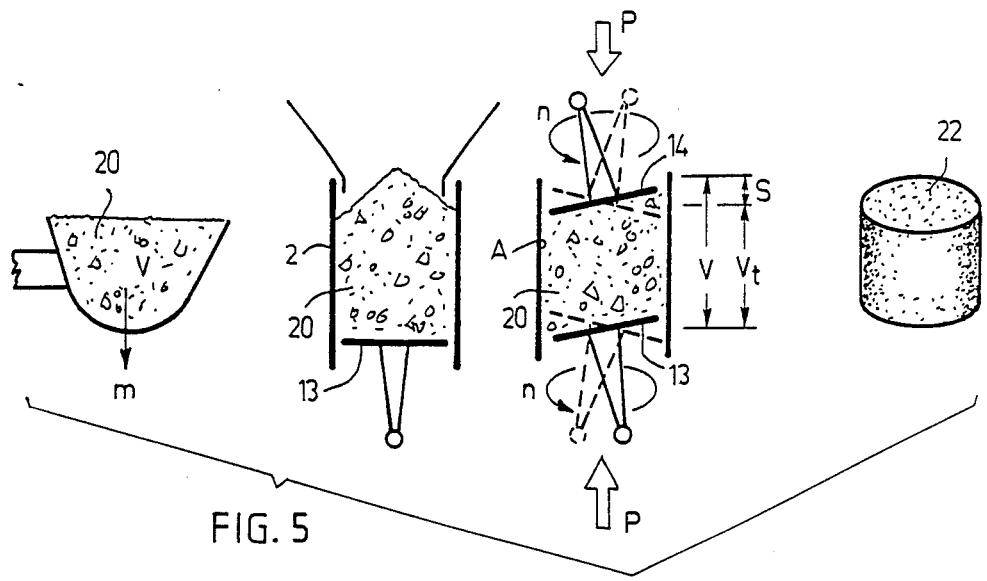
Figure 6:
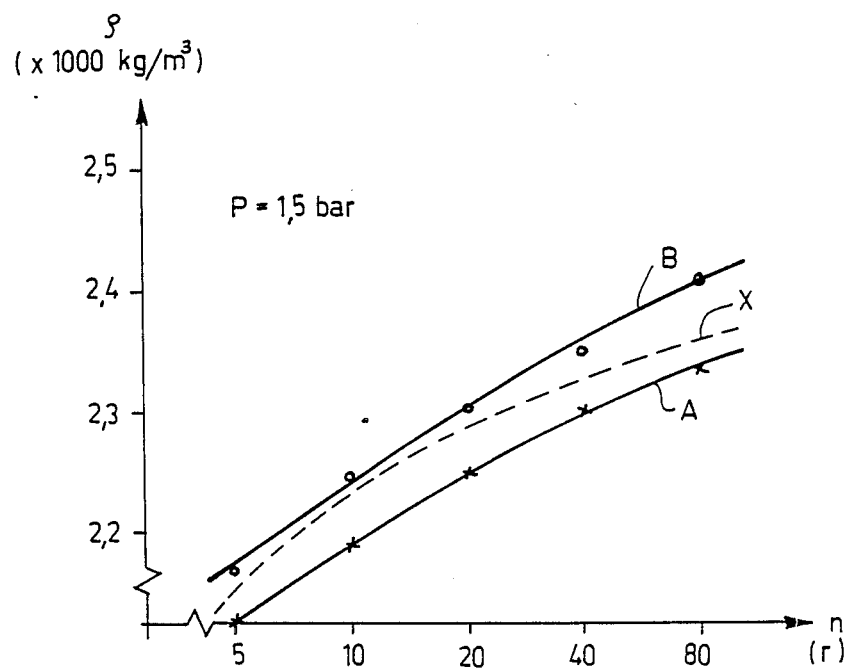

The invention will be described more closely in the following with reference to the attached drawings, wherein FIG. 1 is a detailed front view of the construction of an apparatus according to the invention in a filling position, FIGS. 2 and 3 are sectional views of the apparatus along the lines II—II and III—III respectively in FIG. 1, FIG. 4 is an enlarged axial section of a compaction container of the apparatus and compaction pistons thereof in an operative position, FIG. 5 illustrates different operational stages of the method according to the invention, FIG. 6 is an example of a compactibility measurement of a concrete mass carried out by means of the apparatus.

The apparatus illustrated in FIGS. 1-4 comprises a vertical compaction cylinder 2 fastened on a frame 1 and a lower compaction piston 3 fastened on a rotatable vertical shaft 4 to close the lower end of the cylinder. A vertical shaft 6 is rotatably mounted on a carriage 5 which is vertically slidably mounted on the frame above the compaction cylinder. An upper compaction piston 7 is fastened to said shaft 6 to close the upper end of the compaction cylinder. The vertical shaft 6 is fastened on a piston rod of a hydraulic cylinder 8 mounted on the frame, by means of which piston rod the carriage and the piston thereof are vertically displaceable.

The base of the frame supports a gear box 9 which is connected to the vertical shaft 4 of the lower compaction piston and the vertical shaft 6 of the upper compaction piston by means of an intermediate shaft 10 and transmission wheels 11 so that both vertical shafts rotate with the same speed. The gear box is rotated by an electric motor 12.

Each compaction piston forms a round plate 13 and 14 respectively, which is slantingly positioned with respect to the vertical shaft. Both pistons are mounted on the shafts obliquely in such a manner that the plates 13, 14 thereof are positioned in parallel with each other, as appears from FIGS. 1 and 2.

The apparatus further comprises a meter board 15 provided with e.g. indicators 16-18 for the pressure of the hydraulic cylinder 8, the number of revolutions of the compaction pistons and the displacement of the carriage. A scale 19 is attached to the side of the frame to directly indicate the vertical position of the carriage.

FIG. 5 illustrates a method of measurement performed by means of the apparatus.

A sample 20 having a pre-determined mass m is taken from the concrete mass. The sample is poured into the compaction cylinder 2 having a cross-sectional area F and the upper compaction piston 7 is lowered on the sample. The piston is pressed against the sample by means of the hydraulic cylinder with a constant force P. Thereafter the pistons are rotated by means of the electric motor, whereby the plates 13, 14 thereof, which are mounted in a slanting position, direct a shearing compaction effect on the sample. As a result thereof, the sample is compacted after a pre-determined number of revolutions n of the pistons over a distance S which can be read also from the scale 19, the volume of the sample changing into a value $V_t$. The compacted sample can be removed as a cylindrical test piece 22 from which the strength properties of the concrete mass are calculated after curing.

The electric motor is controlled by a freely selectable program so that it stops at pre-determined intervals to read the numbers of revolutions n and the corresponding depressions S. Alternatively, the electric motor can be rotated continuously, the numbers of revolutions of the pistons and the depressions being continuously transferred to the memory of a process unit 23 in order to illustrate the compactibility of the sample by means of a recorder 21.

The compactibility of the sample can be illustrated graphically as a density value of the sample as a function of the number of revolutions of the pistons, i.e. as a function of the compaction impulses. FIG. 6 shows an example of one way of controlling the compactibility of concrete. A curve A in the Figure illustrates the change of the density of a sample taken from the concrete mass as the compaction proceeds when the sample is exposed to shear compaction by means of the apparatus described earlier under the influence of a constant compression pressure P=1.5 bar. The water/cement ratio w/c of the concrete mass represented by the curve A was 0.328.

The curve B correspondingly illustrates the results of a test performed with the same concrete mass, the water/cement ratio being 0.361. In other respects the mass is identical in these two tests.

In this example, the casting machine succesfully performed the casting process by means of these two concrete masses. Experiences indicate that this concrete casting will succeed also with other kinds of concrete masses, provided that their compacting properties fall within the curves A and B when the measurement is carried out according to the invention.

By means of the method according to the invention it is possible to quickly, i.e. in some tens of seconds, measure the compactibility of a concrete mass which is being manufactured, thus obtaining reliable information on the applicability of the concrete mass to the casting work in each particular case by means of a certain casting machine.

The drawings and the description related thereto are only intended to illustrate the idea of the invention. The method and the apparatus according to the invention may vary within the scope of the claims. The invention is also suitable for measuring of the properties of other masses similar to fresh concrete, such as e.g. in the manufacture of bricks, and for the measurement of certain geodetic properties of soil.

I claim:

1. Method of measuring the properties, in particular the compactibility of a stiff mass to be cast, such as a fresh concrete mass, wherein a sample (20) having a pre-determined weight is taken from the mass, the sample is exposed to a compaction effect, and the magnitude of a compression (S) of the sample and the work used therefore is determined, characterized in that the sample (20) is compressed in two opposite directions with a constant force (P), the sample is subjected to shearing compaction under a constant compression between two slanting planes (13,14) which extend in parallel with each other and alter their position through rotation, and the volume (V and $V_t$) of the sample is measured at the beginning of the compaction and after certain compaction impulses (n).

2. Method according to claim 1, characterized in that the sample (20) is weighed and measured for the determination of the density thereof after the compaction.

3. Method according to claim 2, characterized in that the volume ($V_t$) of the sample (20) and the density thereof respectively is measured as a function of a pre-determined compaction work, such as the rotational motion (n) of said slanting planes (13,14).

4. Method according to claim 1 characterized in that the volume ($V_t$) of the sample (20) and the density thereof respectively is measured as a function of a pre-determined compaction work, such as the rotational motion (n) of said slanting planes (13,14).

5. Method according to claim 1, characterized in that the strength of a test piece (22) formed by the compacted sample (20) is determined after the curing thereof.

6. Apparatus for measuring the properties, in particular the compactibility of a stiff mass to be cast, such as a fresh concrete mass, said apparatus comprising a container (2) for a concrete sample (20) having a pre-determined weight (m), means (8) for compression of the sample, and means (19) for measurement of the compression of the sample, characterized by comprising a compacting device including two compaction plates (13,14), the surfaces of which extend in parallel and which are rotatable around an axis of rotation (4,6) slantingly positioned with respect to the surfaces of the compaction plates in order to direct a shearing compaction on the sample (20) contained in said container (2) from two opposite directions, and means (6,8) for pressing one of the compaction plates towards the other compaction plate.

7. Apparatus according to claim 6, characterized in that said compaction plates (13,14) are formed by pistons (3,7) extending into a cylindrical container (2) from opposite sides, said pistons being mounted on coaxial rotating shafts (4,6) in such a manner that the compaction plates are positioned slantingly with respect to the rotating shafts.

8. Apparatus according to claim 7, characterized in that the rotating shaft (6) of one (7) of the pistons is axially displaceable by means of a pressure-medium operated actuating device (8) in order to press the compaction plate (14) against the sample (20) positioned in the container (2).

9. Apparatus according to claim 8, characterized in that it is provided with an instrument (19) indicating the axial movement of the rotating shaft (6).

10. Apparatus according to claim 8, characterized in that it is provided with an instrument (17) indicating the number of revolutions (n) of the rotating shaft (6).

* * * * *